US012178561B2

(12) United States Patent
Kadbi et al.

(10) Patent No.: US 12,178,561 B2
(45) Date of Patent: Dec. 31, 2024

(54) RESPIRATORY BIOFEEDBACK FOR MRI-GUIDED RADIOTHERAPY

(71) Applicant: KONINKLIJKE PHILIPS N.V., Eindhoven (NL)

(72) Inventors: Mohammad Hossein Kadbi, Houston, TX (US); Lizette Warner, Arlington, TX (US)

(73) Assignee: Koninklijke Philips N.V., Eindhoven (NL)

( * ) Notice: Subject to any disclaimer, the term of this patent is extended or adjusted under 35 U.S.C. 154(b) by 263 days.

(21) Appl. No.: 17/642,971

(22) PCT Filed: Sep. 10, 2020

(86) PCT No.: PCT/EP2020/075257
§ 371 (c)(1),
(2) Date: Mar. 15, 2022

(87) PCT Pub. No.: WO2021/052843
PCT Pub. Date: Mar. 25, 2021

(65) Prior Publication Data
US 2022/0338751 A1  Oct. 27, 2022

Related U.S. Application Data

(60) Provisional application No. 62/903,014, filed on Sep. 20, 2019.

(30) Foreign Application Priority Data

Oct. 8, 2019  (EP) .................................... 19201823

(51) Int. Cl.
*A61B 5/055* (2006.01)
*A61N 5/10* (2006.01)
*G01R 33/56* (2006.01)

(52) U.S. Cl.
CPC ................ *A61B 5/055* (2013.01); *A61N 5/10* (2013.01); *G01R 33/5608* (2013.01); *A61N 2005/1055* (2013.01)

(58) Field of Classification Search
CPC ..... A61B 5/0036; A61B 5/7292; A61B 5/055; A61N 5/10; A61N 5/1068;
(Continued)

(56) References Cited

U.S. PATENT DOCUMENTS

| 5,363,844 A | 11/1994 | Riederer et al. |
| 6,279,579 B1 | 8/2001 | Riaziat et al. |

(Continued)

FOREIGN PATENT DOCUMENTS

| EP | 3456383 A1 | 3/2019 |
| WO | 2012049634 A1 | 4/2012 |

(Continued)

OTHER PUBLICATIONS

Krueger S, Nielsen T. Efficient respiratory navigator-based 4D MRI. ISMRM Annual Meeting. 2016;24rd (3549).
(Continued)

*Primary Examiner* — Joel Lamprecht
*Assistant Examiner* — Nyrobi Celestine

(57) ABSTRACT

A medical system (100, 500) includes: a radiotherapy system (102) configured for controllably irradiating a target volume (114) within an irradiation zone (112); a subject support (120) configured for supporting at least a ventral region (124) of a subject (122) within the irradiation zone; a breath monitor system (132, 132') configured for providing a motion signal (154, 158) descriptive of subject breathing motion; and a subject display (130, 130') configured for displaying a breathing phase indicator (160, 160') to the subject when supported by the subject support. Execution of
(Continued)

the machine executable instructions (150) causes a processor (142) to carry out certain functions of the medical system.

17 Claims, 7 Drawing Sheets

(58) Field of Classification Search
CPC .......... A61N 2005/1055; G01R 33/567; G01R 33/5608; G01R 33/4808
See application file for complete search history.

(56) References Cited

U.S. PATENT DOCUMENTS

| | | | |
|---|---|---|---|
| 6,937,696 | B1 | 8/2005 | Mostafavi |
| 2002/0091314 | A1 | 7/2002 | Schlossbauer et al. |
| 2004/0116804 | A1* | 6/2004 | Mostafavi ............ A61B 6/5288 600/428 |
| 2011/0181285 | A1 | 7/2011 | Greiser |
| 2011/0201916 | A1 | 8/2011 | Duyn et al. |
| 2013/0035588 | A1* | 2/2013 | Shea ................ G01R 33/56308 600/413 |
| 2016/0081588 | A1* | 3/2016 | Zeller ....................... G06T 5/73 382/131 |
| 2017/0328970 | A1* | 11/2017 | Bi .......................... A61B 5/055 |
| 2019/0080459 | A1* | 3/2019 | Lachaine ............. A61N 5/1049 |
| 2020/0238102 | A1* | 7/2020 | Lamb ..................... G16H 20/40 |
| 2022/0008751 | A1* | 1/2022 | Sadeghi ............... A61N 5/1049 |

FOREIGN PATENT DOCUMENTS

| | | |
|---|---|---|
| WO | 2015117084 A1 | 8/2015 |
| WO | 2017129454 A1 | 8/2017 |

OTHER PUBLICATIONS

Glide-Hurst CK, Kim JP, To D, et al. Four dimensional magnetic resonance imaging optimization and implementation for magnetic resonance imaging simulation. Pract Radiat Oncol.2015;5(6):433-42.

Li G, Caraveo M, Wei J, et al. Rapid estimation of 4DCT motion-artifact severity based on 1D breathing-surrogate periodicity. Med Phys. 2014;41(11):111717.

To, David T. , Kim, Joshua P. , et al. Impact of incorporating visual biofeedback in 4D MRI, Journal of Applied Clinical Medical Physics (vol. 17 issue 3 pp. 128-137 ).

Li G, Cohen P, Xie H, et al. A novel four-dimensional radiotherapy planning strategy from a tumor-tracking beam's eye view. Phys Med Biol. 2012;57(22):7579-7598.

Lee Danny et al "Audiovisual Biofeedback Improves Cine-Magnetic Resonance Imaging Measured Lung Tumor Motion Consistency" Int. Journal of Radiation vol. 94, No. 3 , Nov. 18, 2015 p. 628-636.

International Search Report and Written Opinion from PCT/EP2020/075257 mailed Dec. 3, 2020.

* cited by examiner

RESPIRATORY BIOFEEDBACK FOR MRI-GUIDED RADIOTHERAPY

CROSS REFERENCE TO RELATED APPLICATIONS

This application is a U.S. national phase application of International Application No. PCT/EP2020/075257 filed on Sep. 10, 2020, which claims the benefit of EP Application Serial No. 19201823.2 filed on Oct. 8, 2019 and U.S. Application Ser. No. 62/903,014 filed on Sep. 20, 2019, both of which are incorporated herein by reference.

FIELD OF THE INVENTION

The invention relates to radiotherapy, in particular to the guidance of radiotherapy using magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a patient. Such medical images may be useful for planning and/or guiding a radiotherapy system.

The journal article To et. al., "Impact of incorporating visual biofeedback in 4D MRI," J. Applied Clinical Med. Phys, vol. 17, pp. 128-137 (2016) https://doi.org/10.1120/jacmp.v17i3.6017 discloses that precise radiation therapy (RT) for abdominal lesions is complicated by respiratory motion and suboptimal soft tissue contrast in 4D CT. 4D MRI offers improved contrast although long scan times and irregular breathing patterns can be limiting. To address this, visual biofeedback (VBF) was introduced into 4D MRI.

SUMMARY OF THE INVENTION

The invention provides for a medical system, a computer program product, and a method in the independent claims. Embodiments are given in the dependent claims.

Embodiments may provide for an improved means of guiding a radiotherapy system using a previously acquired magnetic resonance imaging data set. This may be achieved by using a time resolved magnetic resonance imaging data set (a 4D MRI data set) that is referenced or synchronized to a measured motion signal of a breath monitor system. During the radiotherapy a current motion signal is measured with the breath monitor system. A display provides a rendering of a breathing phase indicator. The breathing phase indicator shows a difference between a desired motion signal and the current motion signal. The breathing phase indicator provides a biofeedback signal that the subject can use to better control and match the breathing pattern that the subject had when the time resolved magnetic resonance imaging data set was acquired.

In one aspect the invention provides for a medical system that comprises a radiotherapy system configured for controllably irradiating a target volume within an irradiation zone. The irradiation zone as used herein encompasses a volume in space to which the radiotherapy system can steer or focus the target volume. The medical system further comprises a subject support configured for supporting at least a ventral region of a subject within the irradiation zone. The ventral region may encompass an abdominal and/or thoracic region of the subject.

The medical system further comprises a breath monitor system that is configured for providing a motion signal descriptive of subject breathing motion. The breath monitor system may be any system that is able to measure the motion of a subject as the subject breathes. For example, the motion signal may provide a breathing phase of the subject. The medical system further comprises a subject display configured for displaying a breathing phase indicator to the subject supported by the subject support. The breathing phase indicator as used herein may be an indicator that is rendered on the subject display and communicates a current breathing phase or motion of the subject.

The medical system further comprises a memory storing machine-executable instructions. The medical system further comprises a processor configured for controlling the medical system. Execution of the machine-executable instructions causes the processor to receive a time resolved magnetic resonance imaging dataset. The time resolved magnetic resonance imaging dataset may be a series of magnetic resonance images in one example. In another example the time resolved magnetic resonance imaging dataset may be an average image for a particular time or breathing phase range.

In another example the time resolved magnetic resonance imaging dataset is magnetic resonance imaging data that has been pre-processed to indicate the location of various anatomical structures of a subject as a function of time or breathing phase. The time resolved magnetic resonance imaging dataset is synchronized to a measured motion signal. The measured motion signal is cyclical in time. The measured motion signal may be equivalent to the motion signal which may be provided by the breath monitor system. The time resolved magnetic resonance imaging dataset therefore provides time resolved magnetic resonance imaging data as a function of the motion signal.

Execution of the machine-executable instructions further causes the processor to repeatedly determine a desired motion signal by temporally stepping through the measured motion signal. For example, the measured motion signal may have a particular waveform or structure as a function of time or period. The desired motion signal can be taken from the measured motion signal by breaking the measured motion signal into discreet time periods or chunks and then recalling them sequentially. Execution of the machine-executable instructions further causes the processor to repeatedly acquire a current motion signal using the breath monitor system. The current motion signal may be a motion signal that is measured at a present time point.

Execution of the machine-executable instructions further causes the processor to repeatedly render the breathing phase indicator on the display. The breathing phase indicator is configured to indicate the difference between the desired motion signal and the measured motion signal the breathing phase indicator therefore provides a biofeedback signal to the subject and indicates the difference between the desired breathing pattern and the current breathing pattern. Execution of the machine-executable instructions further causes the processor to repeatedly generate control commands configured for controlling the targeting of the radiotherapy system using a first portion of the time resolved magnetic resonance imaging dataset synchronized to the desired motion signal or a second portion of the time resolved magnetic resonance imaging dataset referenced to the current motion signal.

The control commands are generated to match one of two groups of the time resolved magnetic resonance imaging dataset. The first portion is the portion which corresponds to the current desired motion signal. If however the subject deviates from the desired motion signal by too much then it would be inaccurate to target or control the radiotherapy system using this signal. In this case the current motion signal is then used to reference the time resolved magnetic resonance imaging dataset and obtain data which can be used for properly targeting the radiotherapy system.

In this embodiment the data from a previous magnetic resonance imaging scan is provided in the form of a time resolved magnetic resonance imaging dataset and this is referenced by the measured motion signal. The displaying of the breathing phase indicator assists the subject in matching the breathing pattern that was used for the acquisition of the time resolved magnetic resonance imaging dataset. If the subject follows the same breathing pattern then it is very accurate to use the time resolved magnetic resonance imaging dataset to predict in the future where the subject's various internal organs will be positioned. If the subject on the other hand has an erratic breathing pattern then it becomes very difficult to properly predict how the subject will move in the future. Embodiments may therefore provide for an improved targeting within the subject for a radiotherapy system.

In another embodiment the time resolved magnetic resonance imaging dataset is descriptive of the at least a ventral region of the subject supported within the irradiation zone.

In another embodiment the control commands configured to select between the first portion of the time resolved magnetic resonance imaging dataset and the second portion of the time resolved magnetic resonance imaging dataset by applying a predetermined criterion to a match between the current motion signal and the measured motion signal. For example, if the current motion signal deviates from the measured motion signal by more than the predetermined criterion then the system could switch to the second portion of the time resolved magnetic resonance imaging data set. The second portion of the time resolved magnetic resonance imaging data set could for example be chosen as a time offset so that the current motion signal fits to the measured motion signal within the predetermined criterion again.

The term "synchronized to" may indicate that the current motion signal is synchronized to or locked to the desired motion signal. The term "referenced to" may also indicates that the current motion signal is synchronized to or locked to the desired motion signal with a time or phase offset.

The motion signal is the signal measured by the breath monitor system. The desired motion signal is a motion signal derived from a motion signal measured by the breath monitor system. The term "desired" is a label used to indicated a particular motion signal. The current motion signal is also a motion signal measured by the breath monitor system. The term "current" is a label it indicated particular data measured by the breath monitor system.

In another embodiment the medical system further comprises a magnetic resonance imaging system. The magnetic resonance imaging system may be a separate standalone magnetic resonance imaging system or the magnetic resonance imaging system may be incorporated into the radiotherapy system.

The memory further contains calibration pulse sequence commands configured for acquiring calibration magnetic resonance data from an imaging zone according to a four-dimensional magnetic resonance imaging protocol. A four-dimensional magnetic resonance imaging protocol encompasses herein a magnetic resonance imaging protocol that acquires data three-dimensionally in a spatial manner and one additional dimension in time so a four-dimensional magnetic resonance imaging protocol acquires three-dimensional magnetic resonance imaging data as a function of time.

Execution of the machine-executable instructions further causes the processor to acquire the measured motion signal with the breath monitor system for a predetermined duration. For example, the subject may be inserted into the magnetic resonance imaging system and the breathing of the subject may be monitored using the breath monitor system. Execution of the machine-executable instructions further causes the processor to control the magnetic resonance imaging system with the calibration pulse sequence commands to acquire the calibration magnetic resonance data. The calibration magnetic resonance data is divided into movement phase bins. The measured motion signal may for example be used to divide the acquired data into the movement phase bins. Execution of the machine-executable instructions further cause the processor to reconstruct the time resolved magnetic resonance imaging dataset from the calibration magnetic resonance data.

Execution of the machine-executable instructions further causes the processor to repeatedly perform the following during the acquisition of the calibration magnetic resonance data: determine a temporary desired motion signal by temporally stepping through the measured motion signal, acquire a calibration motion signal using the breath monitor system, binning the magnetic resonance imaging data into the movement phase bins and using the calibration motion signal, and then finally rendering the breathing phase indicator on the display. The breathing phase indicator is again configured to indicate the difference between the temporary motion signal and the calibration motion signal. In this embodiment the feedback is provided to the subject in the same way as it was during the radiotherapy step. This may be beneficial because if the subject is able to control his or her breathing more regularly then the quality of the magnetic resonance imaging data will be improved because the subject's motion is more repeatable.

If during the magnetic resonance imaging phase and the radiotherapy phase the same sort of patient motion monitoring and biofeedback is provided then both the quality of the time resolved magnetic resonance imaging data will be improved as well as more accurate targeting by the radiotherapy system.

In another embodiment the magnetic resonance imaging system is integrated into the radiotherapy system. The irradiation zone is within the imaging zone. A consequence of the irradiation zone being within the imaging zone is that the magnetic resonance imaging system can be used for guiding or targeting for the radiotherapy system. In this case the subject display and the breath monitor system of the radiotherapy system and the magnetic resonance imaging system may be identical.

In another embodiment the memory further contains imaging pulse sequence commands. Execution of the machine-executable instructions further cause the processor to acquire imaging magnetic resonance data by controlling the magnetic resonance imaging system with the imaging pulse sequence commands during generation of the control commands. Execution of the machine-executable instructions further causes the processor to reconstruct at least one magnetic resonance image from the imaging magnetic resonance data. The breathing phase indicator is fully configured for displaying the at least one magnetic resonance image. For example, the breathing phase indicator may display the actual magnetic resonance image to the subject as an aid for the subject in controlling his or her breathing pattern.

In another embodiment the irradiation zone and the imaging zone are disjoined. The consequence of this is that the magnetic resonance imaging system cannot be used for directly guiding the radiotherapy system. In this case the radiotherapy system may be in one location and the magnetic resonance imaging system may be in a different location. For example, the subject may first be placed into the magnetic resonance imaging system to provide the time resolved magnetic resonance imaging dataset and the measured motion signal. The subject can then be physically moved to the radiotherapy system. This may have the benefit of combining the magnetic resonance imaging system and the radiotherapy system into a single medical system that functions together cooperatively. In this example the radiotherapy system may have a first breath monitor system and a first subject display and the magnetic resonance imaging system may have a second breath monitor system and a second subject display.

In another embodiment the breathing phase indicator is configured for displaying the desired motion signal as a waveform. The breathing phase indicator is fully configured for displaying the current motion signal as a location relative to the waveform. For example, there may be a cursor which indicates the current breathing phase of the subject and this is compared to the desired motion signal. This may be useful in indicating to the subject if they have the correct breathing phase or not. The waveform may also display the maximum and minimum breathing phase. This may be useful to signal to the subject if they are hyperventilating or are breathing heavier than they did when the measured motion signal was acquired.

In another embodiment the breathing phase indicator is configured for displaying the desired motion signal as a location of a first object. The breathing phase indicator is further configured for displaying the current motion signal as a position of a second object. For example, they may be two circles or other geometric shapes. The subject may have an easier time trying to adjust his or her breath pattern so that the two objects overlap or are within an acceptable distance of each other.

In another embodiment the breathing phase indicator is configured for controlling an animation of a subject using the designed motion signal and the current motion signal. The animation for instance may be a simplification or rendering of a subject position or animation of a person breathing. This may be useful in the subject mirroring the desired motion signal.

In another embodiment execution of the machine-executable instructions further cause the processor to control the radiotherapy system with the control commands. This may be beneficial because it may provide for a radiotherapy session with improved accuracy and effectiveness.

In another embodiment the breath monitor system comprises a respiratory belt.

In another embodiment the breath monitor system comprises an optical respiratory detection system. This for example may be a camera or imaging system.

In another embodiment the breath monitor system comprises an infra-red respiratory detection system. This for example may be an infra-red camera system. An infra-red respiratory detection system may be particularly effective because it may be able to see through clothing or other garments worn by a subject. An example of a commercially available infra-red camera system is the Philips VitalEye system. VitalEye technology and algorithms simultaneously process more than 200 body locations and extract signs of breathing.

In another embodiment the breath monitor system comprises an internal navigator pulse sequence. For example, there may be a magnetic resonance imaging navigator pulse sequence which is used to monitor such things as the diaphragm position.

In another embodiment the display is a projector configured for projecting the breathing phase indicator on a wall.

In another embodiment the display is a projector configured for projecting the breathing phase indicator on a bore of the medical system. For example, if the system provides for a magnetic resonance imaging system there may be a projection onto the inside bore that the subject is able to see.

In another embodiment the display is an LCD display.

In another embodiment the display is a magnetic resonance imaging compatible display. For example, light pipes or other technology may be used to move an indicator or display such that it is visible to the subject.

In another embodiment the radiotherapy system is a linear accelerator (LINAC) radiotherapy system.

In another embodiment the radiotherapy system is a cobalt radiotherapy system. For example, there may be a cobalt radiation source which is used to provide gamma radiation for irradiating a subject.

In another embodiment the radiotherapy system is an X-ray radiotherapy system. For example, an X-ray system may be used for providing radiation for providing the radiotherapy.

In another aspect the invention provides for a method of operating a medical system. The medical system comprises a radiotherapy system configured for controlling irradiating a target volume within a radiation zone. The medical system further comprises a subject support configured for supporting at least a ventral region of a subject within the radiation zone. The medical system further comprises a breath monitor system configured for providing a motion signal descriptive of the subject breathing motion.

The medical system further comprises a subject display configured for displaying a breathing phase indicator to the subject supported by the subject support.

The method comprises receiving a time resolved magnetic resonance imaging dataset. The time resolved magnetic resonance imaging dataset is synchronized to a measured motion signal. The measured motion signal is cyclical in time. The method further comprises repeatedly determining a desired motion signal by temporally stepping through the measured motion signal. The method further comprises repeatedly acquiring a current motion signal using the breath monitor system. The method further comprises rendering the breathing phase indicator on a display. The breathing phase indicator is configured to indicate a difference between the desired motion signal and the measured motion signal.

The method further comprises repeatedly generating control commands configured for controlling targeting of the radiotherapy system using a first portion of the time resolved magnetic resonance imaging dataset synchronized to the desired motion signal or a second portion of the time resolved magnetic resonance imaging dataset referenced by the current motion signal.

In another aspect the invention provides for a computer program product comprising machine-executable instructions for execution by a processor controlling a medical system. The medical system comprises a radiotherapy system configured for controllably irradiating a target volume within an irradiation zone. The medical system further comprises a subject support configured for supporting at least a ventral region of a subject within the irradiation zone. The medical system further comprises a breath monitor system configured for providing a motion signal descriptive of the subject breathing motion. The medical system further comprises a subject display configured for displaying a breathing phase indicator to the subject supported by the subject support.

Execution of the machine-executable instructions causes the processor to receive a time resolved magnetic resonance imaging dataset. The time resolved magnetic resonance imaging dataset is synchronized to a measured motion signal. The measured motion signal is cyclical in time. Execution of the machine-executable instructions further causes the processor to repeatedly determine a desired motion signal by temporally stepping through the measured motion signal. Execution of the machine-executable instructions further causes the processor to repeatedly acquire a current motion signal using the breath monitor system.

Execution of the machine-executable instructions further cause the processor to repeatedly render the breathing phase indicator on the display. The breathing phase indicator is configured to indicate a difference between the desired motion signal and the measured motion signal. Execution of the machine-executable instructions further cause the processor to repeatedly generate control commands configured for controlling targeting of the radiotherapy system using a first portion of the time resolved magnetic resonance imaging dataset synchronized to the desired motion signal or a second portion of the time resolved magnetic resonance imaging dataset referenced by the current motion signal.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon. Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
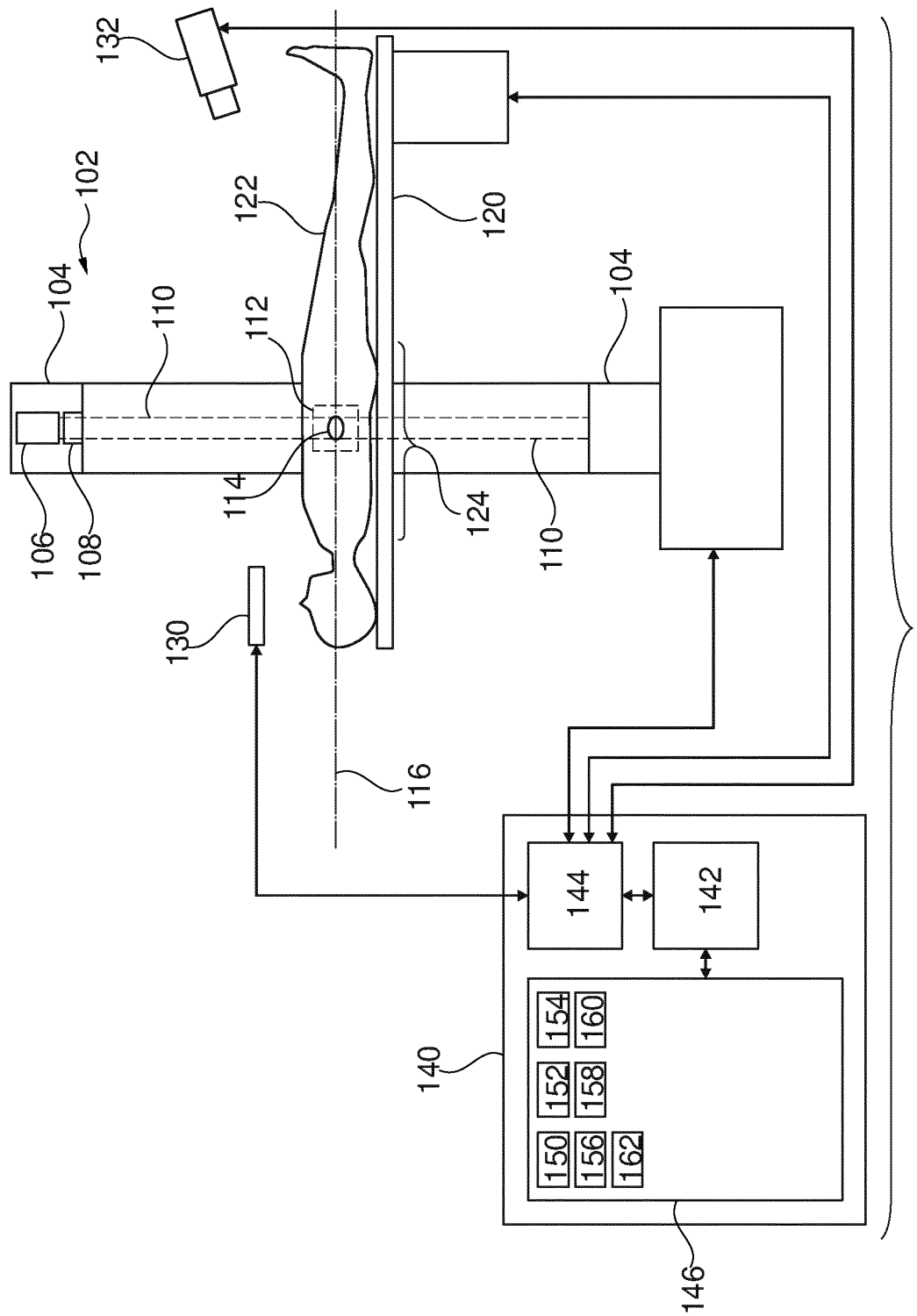
FIG. 1 illustrates an example of a medical system.

FIG. 1 illustrates an example of a medical system 100. The medical system 100 in FIG. 1 comprises a radiotherapy system 102. The radiotherapy system 102 is intended to be representative of one of many different types of radiotherapy systems such as a cobalt radiotherapy system, an X-ray radiotherapy system and a LINAC. In this example the radiotherapy system 102 comprises a gantry 104 with a radiotherapy source 106. A collimator 108 may be used to shape a beam path 110. The volume 112 is the irradiation zone and is representative of the volume to which the target volume 114 can be steered. For example, the collimator 108 may be used to adjust the beam path 110. The gantry 104 has an axis of rotation 116 which rotates the radiotherapy source 106 about.

The medical system 100 further comprises a subject support 120 for supporting a subject 122. The subject support 120 is configured such that it can support a ventral region 124 of the subject 122 in the volume 112.

The medical system 100 is further shown as comprising a display 130 and a breath monitor system 132. In this example the breath monitor system 132 is a camera or infra-red camera. Movement of the subject's 122 chest may be used to generate a motion signal. In this example there is no high magnetic field so the type of display 130 is very open. It could for example be an LCD display, a CRT display, or a virtual reality display or other projection that may be visible to the subject 122.

The radiotherapy system 102, the subject support 120, the display 130 and the breath monitor system 132 are all shown as being connected to a hardware interface 144 of a computer system 140. The subject support 120 may for example contain actuators or motors for adjusting the height and position of the subject 122 relative to the axis of rotation 116.

The computer system 140 further contains a processor 142. The processor 142 is intended to be representative and may be one or more processor cores within a single computer system 140 or it may be multiple cores and processors distributed in multiple computer systems. The processor 142 is connected to the hardware interface 144 which enables the processor 142 to control and operate the radiotherapy system 102. The processor 142 may be optionally connected to a user interface which is not illustrated. The processor 142 is further shown as being connected to a memory 146. The memory 146 is intended to be representative and represent any combination of memory which is accessible to the processor 142.

The memory 146 is shown as containing machine-executable instructions 150. The machine-executable instructions enable the processor 142 to control the operation and function of the radiotherapy system 102. The machine-executable instructions 150 may also enable the processor 142 to perform data processing and numerical tasks. The memory 146 is further shown as containing time resolved magnetic resonance imaging dataset 152. This may be magnetic resonance imaging data in a raw form comprising a four-dimensional magnetic resonance imaging data. In other examples the time resolved magnetic resonance imaging dataset 152 may be pre-processed data for example, it may indicate the location of organs and various positions of the subject 122 as a function of a measured motion signal 154.

The time resolved magnetic resonance imaging dataset 152 is referenced to a measured motion signal 154. This means that the time resolved magnetic resonance imaging dataset 152 is also resolved with respect to a breathing phase of the subject 122. It is not shown in this diagram but the subject support 120 may comprise a radiotherapy couch which for example may have restraints or fixtures for repeatedly positioning the subject 122. Magnetic resonance imaging systems and may also have an equivalent radiotherapy couch which is also not illustrated.

The memory 146 is further shown as comprising a desired motion signal 156. The desired motion signal 156 is a motion signal which is determined by stepping through the measured motion signal 154 sequentially as a function of time. For example, the subject 122 may be placed into the radiotherapy system 102 and for a brief time the breathing phase of the subject 122 may be measured with the breath monitor system 132. After a period of time the processor 142 then synchronizes the measured motion signal 154 with a current motion signal 158 that is measured by the breath monitor system 132. This results in a desired motion signal 156 being generated forward in time by predicting the current motion signal 158 with the previously measured motion signal 154. The processor 142 may receive the current motion signal 158 from the breath monitor system 132. The processor 142 may calculate a breathing phase indicator 160. The breathing phase indicator 160 may then be rendered on the display 130. The breathing phase indicator 160 may be used to display a difference between the current motion signal 158 and the desired motion signal 156. The memory 146 is further shown as containing control commands 162.

The control commands 162 are used to control the radiotherapy system 102 to irradiate the target volume 114. The control commands 162 may be generated in one of two ways. If the current motion signal 158 is tracking the desired motion signal 156 sufficiently well, then the desired motion signal 156 can be used to predict the future position of the subject 122 and this may improve the positioning of the target volume 114. If, however the current motion signal 158 and the desired motion signal 156 differ by too much then the processor 142 may use the current motion signal 158 to determine the targeting position of the target volume 114. The targeting for example can be used by recalling a portion of the time resolved magnetic resonance imaging dataset 152 which corresponds to either the desired motion signal 156 or the closest current motion signal 158.

Figure 2:
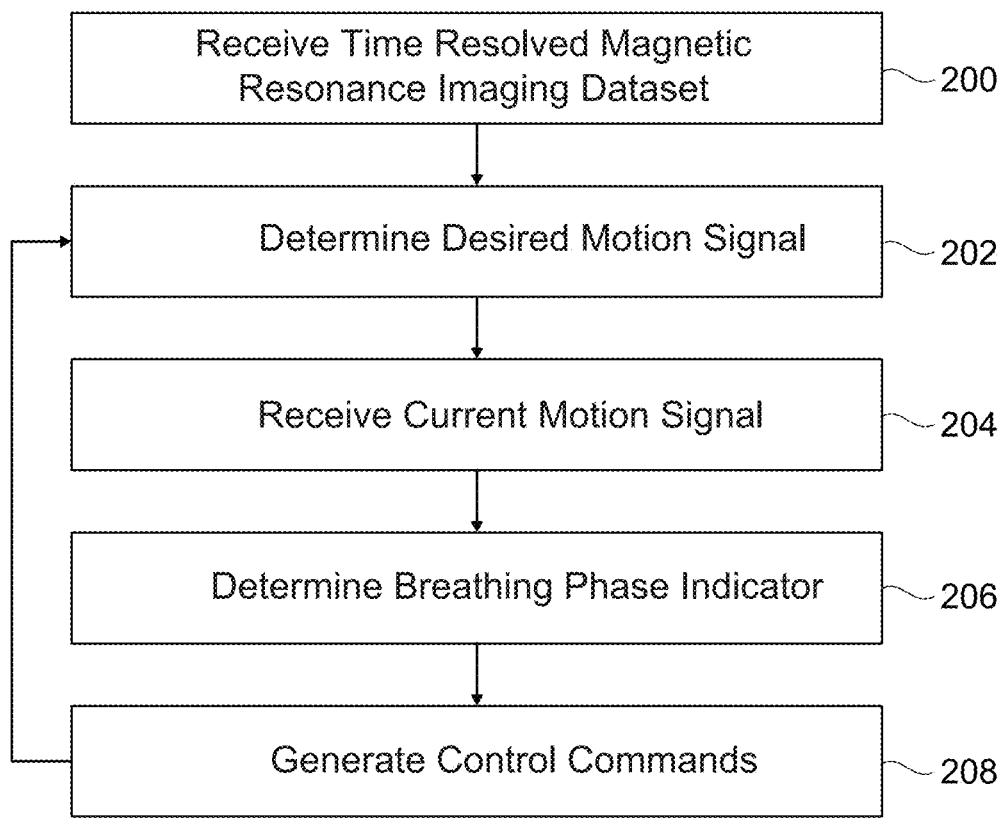
FIG. 2 shows a flow chart which illustrates an example method of operating the medical system of FIG. 1.

FIG. 2 shows a flowchart which illustrates a method of operating the medical system 100 of FIG. 1. First in step 200 the processor 142 receives the time resolved magnetic resonance imaging dataset 152 and the measured motion signal 154. Steps 202, 204, 206, 208 may be repeated in a loop. Next in step 202 the desired motion signal 156 is determined by temporally stepping through the measured motion signal 154. Then in step 204, a current motion signal 158 is received from the breath monitor system 132. Then in step 206 the breathing phase indicator 160 is determined using the desired motion signal 156 and the current motion signal 158. This is then rendered on the display 130.

Then in step 208 the control commands 162 are generated. This is either done using a first portion of the time resolved magnetic resonance imaging dataset 152 which corresponds to the time resolved magnetic resonance imaging dataset 152 may for example be used to register the current location of the subject to a radiotherapy treatment plan. The data from the time resolved magnetic resonance imaging dataset 152 may therefore be used to generate the control commands 162 by updating a radiotherapy treatment plan.

Figure 3:
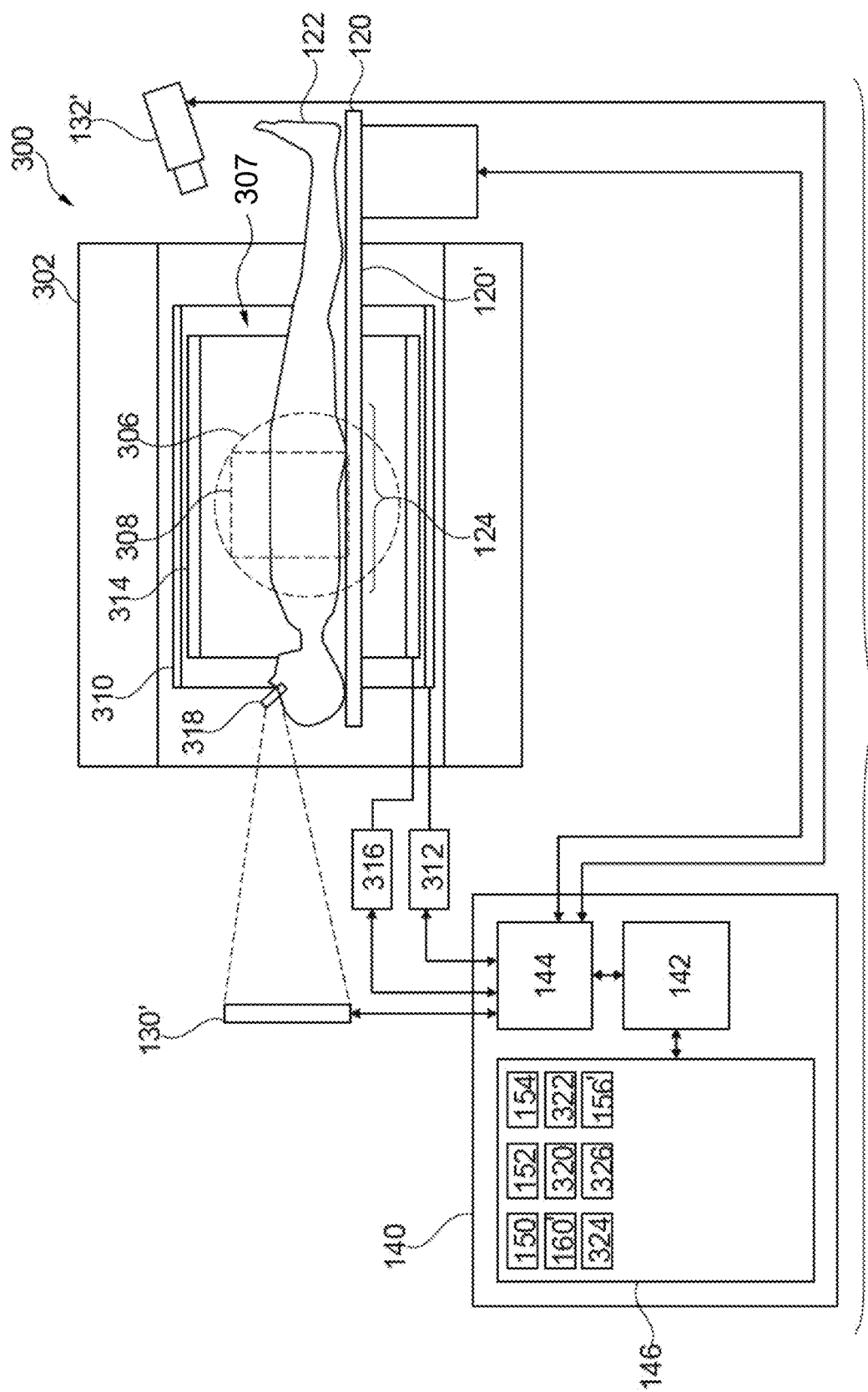
FIG. 3 illustrates additional components of the medical system of FIG. 1.

FIG. 3 illustrates a further view of the medical system 100. The components of FIG. 3 may be combined with the components illustrated in FIG. 1. In this sense the medical system 100 is further shown as comprising a magnetic resonance imaging system 300.

The magnetic resonance imaging system 300 comprises a magnet 302. The magnet 302 is a superconducting cylindrical type magnet with a bore 307 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 307 of the cylindrical magnet 302 there is an imaging zone 308 where the magnetic field is strong and uniform enough to perform magnetic resonance imaging. A field of view 308 is shown within the imaging zone 308. The magnetic resonance data that is acquired acquried for the field of view 308. A subject 122 is shown as being supported by the subject support 120.

Within the bore 307 of the magnet there is also a set of magnetic field gradient coils 310 which is used for acquisition of magnetic resonance data to spatially encode magnetic spins within the imaging zone 308 of the magnet 302. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308.

The radio-frequency coil 314 is illustrated in this example as being a body coil. However, the radio-frequency coil 314 is intended to be representative and may be represented by more than one coil or antenna. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the radio frequency transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The magnetic resonance imaging system 300 is shown as having an additional breath monitor system 132' and a display 130'. In this example the display 130' is positioned outside of the bore 307 and a mirror 318 is positioned so that the subject 122 can view the display 130'. It is now shown in this Fig. but the subject support 120 may be a radiotherapy couch top that is identical with the radiotherapy couch top of the subject support 120 in FIG. 1. This may be used for reproducibly positioning the subject 122 in both the magnetic resonance imaging system 300 and in the radiotherapy system 102.

The radio-frequency transmitter 316 and the magnetic field gradient coil power supply 312 are also shown as being connected to a hardware interface 144 the computer system 140.

The memory 146 is again shown as containing machine-executable instructions. The memory 146 is shown as additionally containing calibration pulse sequence commands 320 that can be used to control the magnetic resonance imaging system 300 to acquire calibration magnetic resonance data according to a four-dimensional magnetic resonance imaging protocol. The memory 146 is further shown as containing the calibration magnetic resonance data 322 that was acquired by controlling the magnetic resonance imaging system 300 with the calibration pulse sequence commands 320. The memory 146 is further shown as containing a measured motion signal 154 that was measured using the additional breath monitor system 132'.

During the acquisition of the calibration magnetic resonance data 322 the measured motion signal 154 could be used to divide the calibration magnetic resonance data 322 into movement phase bins 324. The k-space magnetic resonance imaging data within each of the movement phase bins 324 can then be used to reconstruct the time resolved magnetic resonance imaging dataset 152. The memory is shown as containing a calibration motion signal 326. The calibration motion signal 326 is analogous to the desired measured motion signal 154. The calibration motion signal 326 is also reconstructed from the measured motion signal 154 by stepping through it as a function of time. The memory 146 is shown as containing a breathing phase indicator 160' that is also analogous to the breathing phase indicator 160 of FIG. 1.

Figure 4:
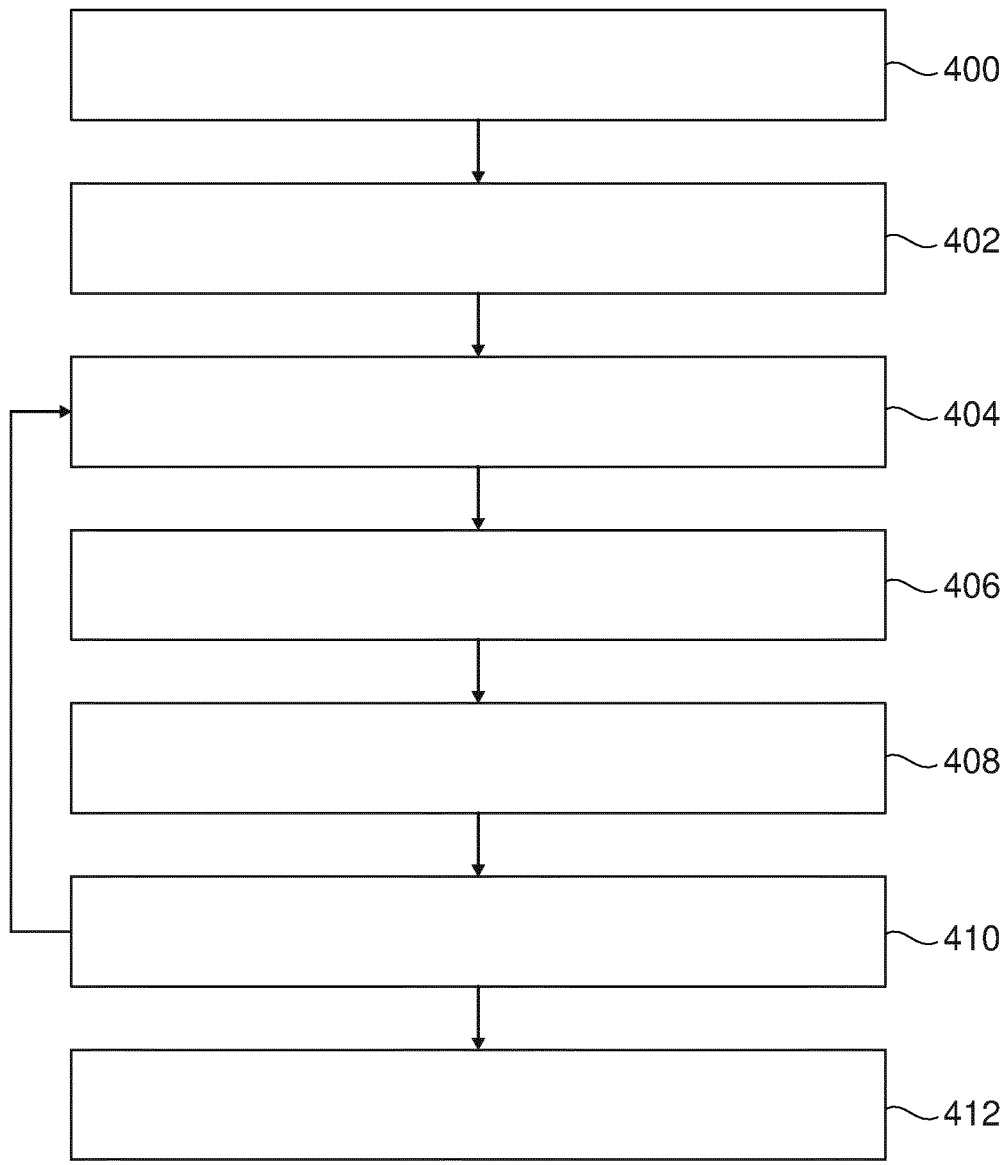
FIG. 4 shows a flow chart which illustrates an example method of operating the components of the medical system illustrated in FIG. 4.

FIG. 4 shows a flowchart which illustrates a method of operating the magnetic resonance imaging system 300 of FIG. 3. First in step 400 the measured motion signal 154 is acquired with the additional breath monitor system 132'. Then in step 412 the magnetic resonance imaging system 300 is controlled with the calibration pulse sequence commands 320 to acquire the calibration magnetic resonance data 322. Steps 404, 406, 408, and 410 are performed repeatedly during the acquisition of the calibration magnetic resonance data 322. In step 404 the temporary desired motion signal 156' is determined by stepping through the measured motion signal 154 temporally.

Next in step 406 the calibration motion signal 326 is acquired with the breath monitor system 132. In step 408 the calibration magnetic resonance data 322 are binned into movement phase bins 324 according to the calibration motion signal 326 or the temporary desired motion signal 156'. In step 410 the breathing phase indicator 160' is constructed using the calibration motion signal 326 and the temporary desired motion signal 156'. This is then rendered on the display 130'. After these steps are performed the method proceeds to step 412 where the time resolved magnetic resonance imaging dataset 152 is reconstructed. It should be noted that some operations such as step 408 may be performed after all of the magnetic resonance imaging data has been acquired.

The methods illustrated in FIGS. 2 and 4 may be combined. For example, the method illustrated in FIG. 4 may be performed first and then the method in FIG. 2 may be performed.

Figure 5:
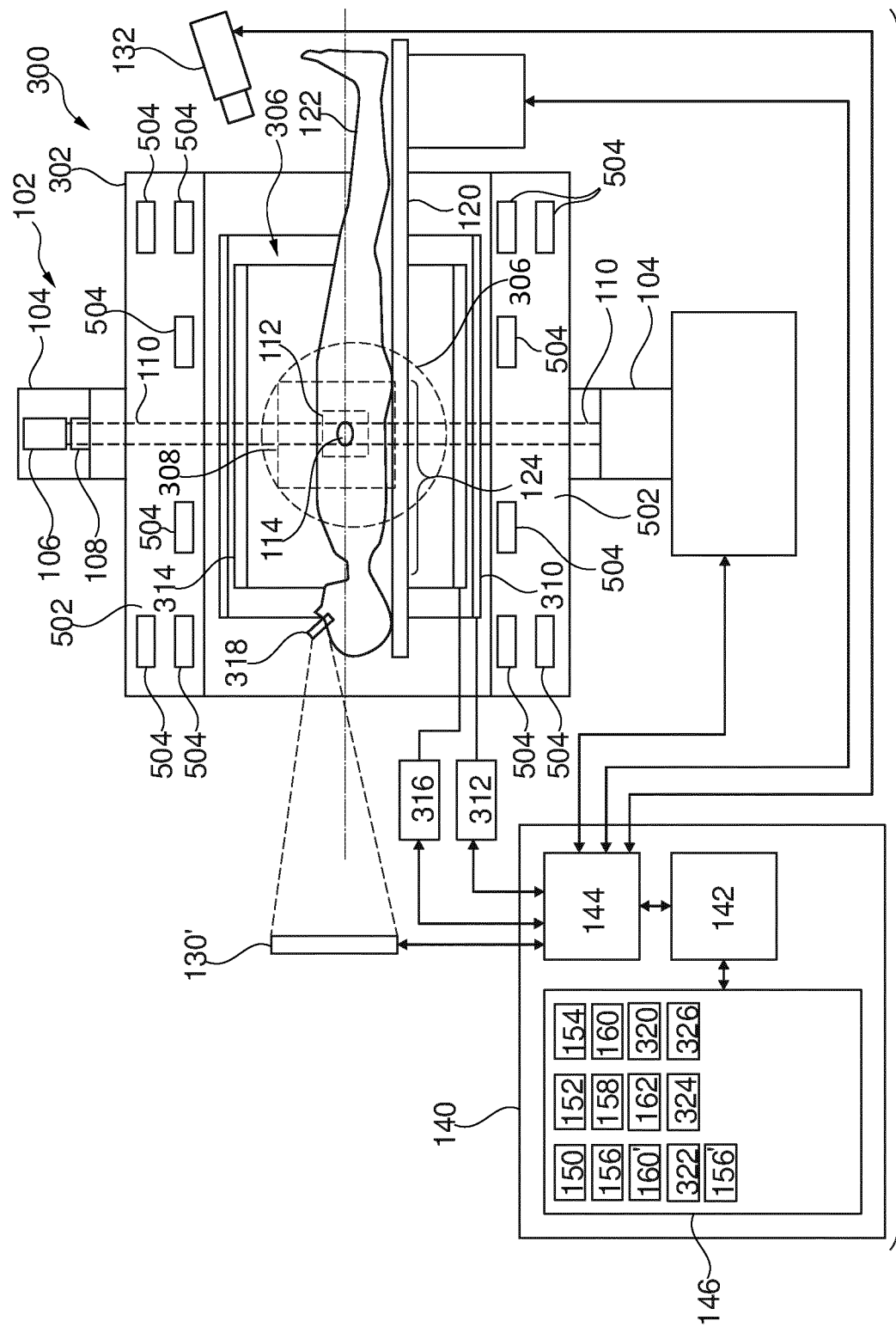
FIG. 5 illustrates a further example of a medical system.

FIG. 5 illustrates a further example of a medical system 500. The example in FIG. 5 combines the features illustrated in FIGS. 1 and 3. The magnetic resonance imaging system 300 and the radiotherapy system 102 are integrated. The volume 112 is within the imaging zone 308. In this example the beam path 110 is shown as passing through a cryostat 502 of the magnet 302. The beam avoids the superconducting coils 504. This is intended to be representative. The magnet 302 may also be replaced with a split coil or open magnet so that the beam path 110 does not pass through it. The methods illustrated in FIGS. 2 and 4 may also be used to operate the medical system 500 of FIG. 5. The method steps of FIG. 4 may be performed first and then the method steps illustrated in FIG. 2 may be performed after this. Additionally, the magnetic resonance imaging system 300 may be used to image the subject 122 during the irradiation of the target volume 114. The magnetic resonance imaging system 300 may therefore also be used to additionally guide the radiotherapy during the irradiation.

Figure 6:
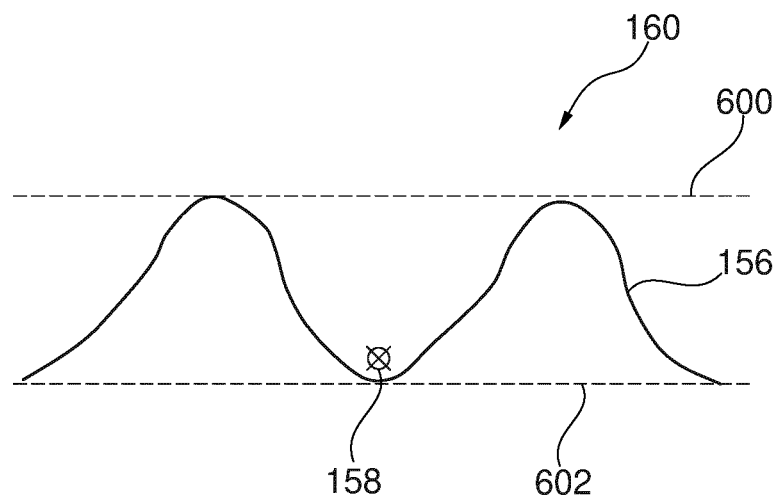
FIG. 6 illustrates an example of a breathing phase indicator

FIG. 6 illustrates an example of a breathing phase indicator 160. The desired motion signal 156 is represented as a repetitive waveform. Marked in this example are a maximum 600 and minimum 602 breathing phase which may be used as a guide for the subject. The current motion signal 158 is indicated as a cursor. The subject tries to adjust his or her breathing so that the cursor stays on the desired motion signal 156.

Figure 7:
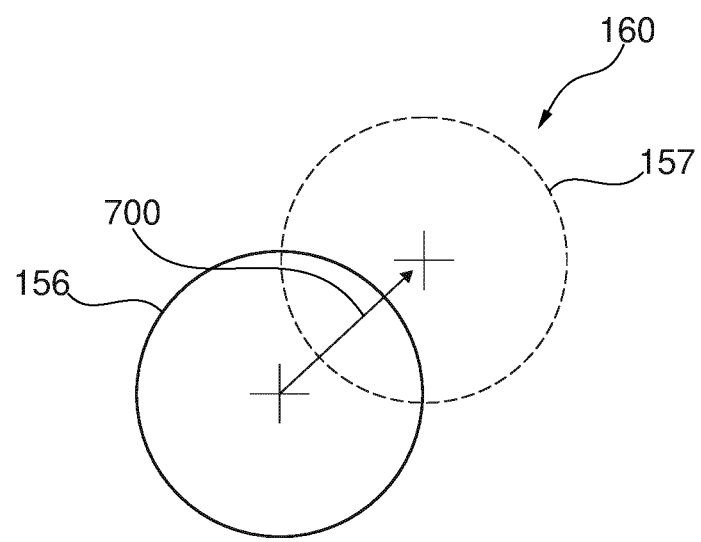
FIG. 7 illustrates a further example of a breathing phase indicator.

FIG. 7 illustrates an alternative example of a breathing phase indicator 160. In this example there are two circles, one circle represents the desired motion signal 156 and the second circle 158 represents a current motion signal. There is a distance 700 between the two which represents a difference between the current motion signal 158 and the desired motion signal 156.

Examples may utilize a respiratory signal (measured motion signal 154 and the current motion signal 158), obtained by a breath monitor system such as a camera. To provide a personalized biofeedback to reduce the motion artefact due to breathing irregularities. This can be done by integrating a motion surrogate or optical motion detection technology with ambient in-bore solution to display the respiratory signal to the patient to guide her/his breathing pattern. Consequently, it is feasible to acquire more accurate and faster 4D MRI image for treatment planning purpose. In addition, the respiratory signal obtained by an optical detection system can be used during the treatment delivery as a personalized biofeedback to maintain the breathing pattern similar to the simulation session to achieve better treatment.

In order to achieve an accurate treatment planning in presence of respiratory motion, 4D CT imaging methods have been use clinically characterize the respiratory motion of the tumor and organs at risks (OARs) in order to minimize radiation toxicity to healthy tissue and maximize radiation to the tumor during radiotherapy. 4D MRI techniques have been under development in the past decade to overcome the limitation of 4D CT such is lack of soft-tissue contrast and excessive ionizing radiation.

It is possible to provide for a prospective amplitude-based 4D MRI to acquire T2-weighted single-shot turbo spin echo (TSE) images at defined phases of the respiratory cycle using common breathing surrogates (breath monitor system 132): an internal navigator or an external bellows. Since this 4D MRI technique is prospectively triggered based on amplitude, long acquisition times were reported due to recurring pauses arising from highly irregular breathing patterns. In addition, irregular breathing pattern, which is very common among sick cancer patients, can cause incorrect sorting of the respiratory phases resulting in binning artefact (aka motion artefact) in the 4D MRI images and discontinuity of the patient anatomy. The prospective 4D MRI may use in some examples an initial 10 seconds training period, in which the program learns the patient-specific breathing parameters and use them to establish the binning levels for the following image acquisition. Although this facilitates the 4D MRI acquisition, it assumes that the next 6-10 minutes breathing follows the training behavior. Therefore, breathing irregularities with greater breathing amplitudes will be ignored. This does not necessarily cause any motion artifacts, but will not faithfully represent the patient breathing behavior. In other words, if the 4D MRI simulation is applied in tumor motion assessment, it may under estimate the irregularities. Therefore, 4D MRI carries the shortcoming of 4D CT since the underline respiratory-correlation method does not contain a mechanism to incorporate breathing irregularity information within the 4D MRI. It is possible to incorporate audio coaching and visual biofeedback into 4D MRI acquisition and radiation therapy delivery improves breathing regularity, increases anatomic reproducibility, and reduces the overall time burden of these procedures.

There are several limitations using internal navigator and external bellows as surrogate for 4D MRI. For external bellow, signal saturation, gain resetting, logistics of setup and positioning time, battery life, and MR bore interference are some limitations. It's been shown that internal navigator is more accurate than the external respiratory bellow signal, however it's difficult to acquire a robust internal navigator signal as the performance is dependent of the operator's expertise in navigator planning as well as internal organ motion. In addition, disruption of imaging can occur if the navigator overlaps with the imaging slices and can cause saturation of imaging volume. As a common problem with both internal navigator and external bellow, the quality of the surrogate signal can highly affect the phase sorting of prospective 4D MRI leading to motion artifact. Motion artifact has been reported causing gross tumor volume (GTV) variation within the breathing cycle of 4D CT in lung cancer by up to 110%, while internal tumor volume (ITV) increased by multi-folds when considering tumor motion trajectory. By minimizing 4D MRI motion artifacts using better respiratory surrogate, the uncertainty in GTV is expected to be reduced.

Examples may comprise a camera that detects motion in the center of the scanner (within the bore 307 of the magnet 302). This motion is analyzed and translated into a respiratory signal (measured motion signal 154 and current motion signal 158). This can be integrated into 4D MR technique to eliminate the limitation of internal navigator or external bellow signal. This system may be more robust and accurate than respiratory bellow signal. In addition, this is an optical system which is interaction free and no operator or patient handling is needed.

There are limitations with current biofeedback systems (breathing phase indicators 160). In some example the respiratory waveform (measured motion signal 154 and the current motion signal 158) for both 4D MRI triggering and biofeedback was derived using two different external surrogates. While both waveforms are based on abdominal motion, ideally, the two systems would be integrated. A simple biofeedback signal (such as an LED display) may not be the best representative of the patient breathing waveform. Ideally, the patient breathing waveform, utilized for phase sorting in 4D MRI technique, can be also used as a biofeedback signal.

A better solution may be the use of an ambient in-bore solution where engaging visuals (breathing phase indicators 160) can be displayed on the back wall and can be seen via a mirror 318 on ahead coil, while the subject 122 can listen to music/sound through the headphone. Here, we propose to display the respiratory signal, obtained by an optical system imaging the patient as a personalized visual biofeedback to guide the patient breathing pattern.

Examples may contain one or more of the following features:
1. An integrated motion surrogate technique or optical technology for a 4D MRI technique to achieve more accurate respiratory surrogate in order to resolve the issues with the current internal and external surrogates.
2. Utilize the respiratory signal, obtained by a motion surrogate technique or an optical system, as a personalized biofeedback to reduce the motion artefact due to breathing irregularities. This can be done by integrating a motion surrogate technique like the optical technology with an ambient in-bore solution to display the respiratory signal to the patient to guide her/his breathing pattern.

By integrating an optical breath monitor system 132 technology into 4D MRI system, it may be possible to acquire more robust and accurate respiratory surrogate signal (measured motion signal 154 current motion signal 158). This accurate surrogate can help to achieve more reliable phase sorting in 4D MRI. In addition, this helps to reduce the idle time in the 4D MRI technique leveraging more robust surrogate and eventually reduce the scan time.

Examples may provide an ambient in-bore solution (for an MRI magnet 302) where engaging visuals can be displayed on the back wall and can be seen via a mirror on the head coil, while the patients can listen to music/sound through the headphone. Here, we propose to display the respiratory signal that is used in 4D MRI, obtained by an optical system or camera, to the patient as a personalized visual biofeedback to guide the patient breathing pattern. The minimum 602 and maximum 600 can be displayed on the monitor on the wall to guide the patient to breath within the lines in order to keep the range of the amplitude of respiratory signal constant. This can help to achieve a regular breathing pattern, which helps to acquire 4D MRI images with better quality and more accurate phase sorting and reduce the motion artifact. In addition, the scan time will be reduced due to regular breathing pattern. This is illustrated in FIG. 8 below.

Figure 8:
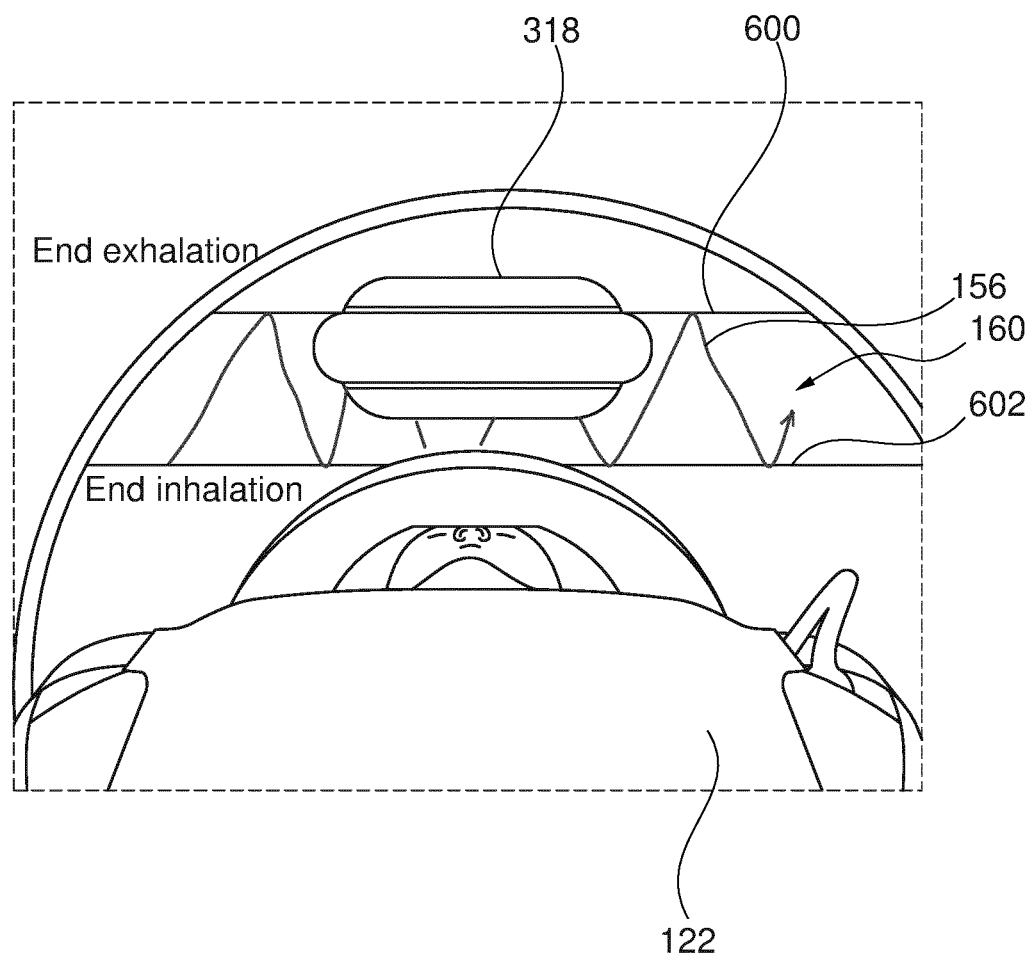
FIG. 8 illustrates a further example of a breathing phase indicator.

FIG. 8 represents a subject 122 in a bore of a medical system. On a wall there is a projection of the breathing phase indicator 160 as is illustrated in FIG. 6. A mirror 318 enables the subject 122 to view this.

FIG. 8: depicts a breath monitor system 132 which uses an infrared camera to obtain a robust respiratory signal to be used as a respiratory surrogate for 4D MRI. The figure provides a schematic of how the respiratory signal obtained by the infra-red camera can be displayed on the wall in on the fly using in-bore solution. The maximum 600 and minimum 602 can be used as a guidance to the patient to breath within the range to keep the breathing amplitude invariable.

On top of acquiring more accurate and faster 4D MRI images, the respiratory signal obtained by an infra-red camera can be also stored in order to use during the treatment session as a personalized biofeedback to maintain the breathing pattern and amplitude similar to the simulation session, when the 4D MRI images are acquired and used for treatment planning.

Examples may be useful for radiotherapy (RT) simulation in any anatomies affected by respiratory motion, particularly for upper abdomen (liver, pancreas) and thorax (lung, esophagus) and also applies to an MR LINAC, CT-simulation or LINAC.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 radiotherpay system
104 gantry
106 radiotherapy source
108 collimator
110 beam path
112 irradiation zone
114 target volume
116 axis of rotation
120 subject support
122 subject
124 ventral region
130 display
130' display
132 breath monitor system
132' breath monitor system
140 computer
142 processor
144 hardware interface
146 memory
150 machine executable instruction
152 time resolved magentic resonance imaging dataset
154 measured motion signal
156 desired motion signal
156' temporary desired motion signal
158 current motion signal
160 breathing phase indicator
160' breathing phase indicator
162 control commands
200 receive a time resolved magnetic resonance imaging dataset synchronized to a measured motion signal
202 determine a desired motion signal by temporally stepping through the measured motion signal
204 acquire a current motion signal using the breath monitor system
206 render a breathing phase indicator on a display
208 generate control commands configured for controlling targeting of the radio therapy system using a first portion of the time resolved magnetic resonance imaging dataset synchronized to the desired motion signal or a second portion of the time resolved magnetic resonance imaging dataset referenced by the current motion signal 300 magnetic resonance imaging system
302 magnet
304 bore of magnet
306 imaging zone
308 field of view
310 magnetic field gradient coil
312 magnetic field gradient coil power supply
314 magnetic resonance antenna
316 transciever
318 mirror
320 calibration pulse sequence commands
322 calibration magnetic resonance data
324 movement phase bins
326 calibration motion signal
400 acquire the measured motion signal with the breath monitor system for a predetermined duration
402 control the magnetic resonance imaging system with the calibration pulse sequence commands to acquire the calibration magnetic resonance data
404 determine a temporary desired motion signal by temporally stepping through the measured motion signal
406 acquire a calibration motion signal using the breath monitor system
408 binning the magnetic resonance imaging data into the movement phase bins using the calibration motion signal
410 render the breathing phase indicator on the display, wherein the breathing phase indicator is configured to indicate a difference between the temporary motion signal and the calibration motion signal
412 reconstruct the time resolved magnetic resonance imaging dataset from the binned calibration magnetic resonance data
500 medical system
502 cryostat
504 superconducting coils
600 maximum
602 minimum
700 distance

The invention claimed is:

1. A medical system comprising:
a magnetic resonance imaging system;
a radiotherapy system configured to controllably irradiate a target volume within an irradiation zone;
a subject support configured to support at least a ventral region of a subject within the irradiation zone;
a breath monitor system comprising a camera, the breath monitoring system being configured to provide a motion signal descriptive of subject breathing motion;
a subject display configured to display a breathing phase indicator to the subject when supported by the subject support;
a memory storing machine executable instructions, wherein the memory further contains calibration pulse sequence commands configured to acquire calibration magnetic resonance data from an imaging zone according to a four-dimensional magnetic resonance imaging protocol; and
a processor;
wherein execution of the machine executable instructions causes the processor to:
acquire a measured motion signal with the breath monitor system for a predetermined duration;
control the magnetic resonance imaging system with the calibration pulse sequence commands to acquire the calibration magnetic resonance data, wherein the calibration magnetic resonance data are divided into movement phase bins,
wherein execution of the machine executable commands further causes the processor to repeatedly perform the following during acquisition of the calibration magnetic resonance data:
determine a temporary desired motion signal by temporally stepping through the measured motion signal;
acquire a calibration motion signal using the breath monitor system;
bin the calibration magnetic resonance data into the movement phase bins using the calibration motion signal, and
render the breathing phase indicator on the subject display, wherein the breathing phase indicator is configured to indicate a difference between the temporary desired motion signal and the calibration motion signal;
wherein execution of the machine executable instruction further causes the processor to reconstruct a time resolved magnetic resonance imaging dataset from the calibration magnetic resonance data;
wherein execution of the machine executable instructions further causes the processor to repeatedly:
determine a desired motion signal by temporally stepping through the measured motion signal;
acquire a current motion signal using the breath monitor system;
render the breathing phase indicator on the subject display, wherein the breathing phase indicator is configured to indicate a difference between the desired motion signal and the current motion signal; and
generate control commands configured to control targeting of the radiotherapy system using a first portion of the time resolved magnetic resonance imaging dataset synchronized to the desired motion signal or a second portion of the time resolved magnetic resonance imaging dataset referenced by the current motion signal wherein the control commands are configured to select between the first portion of the time resolved magnetic resonance imaging dataset and the second portion of the time resolved magnetic resonance imaging dataset by applying a predetermined criterion to a match between the current motion signal and the measured motion signal.

2. The medical system of claim 1, wherein the magnetic resonance imaging system is integrated into the radiotherapy system, wherein the irradiation zone is within the imaging zone.

3. The medical system of claim 2, wherein the memory further contains imaging pulse sequence commands, wherein execution of the machine executable instructions further causes the processor to:
acquire imaging magnetic resonance data by controlling the magnetic resonance imaging system with the imaging pulse sequence commands during generation of the control commands; and
reconstruct at least one magnetic resonance image from the imaging magnetic resonance data, wherein the breathing phase indicator is further configured to display the at least one magnetic resonance image.

4. The medical system of claim 2, wherein the irradiation zone and the imaging zone are disjoined.

5. The medical system of claim 1, wherein the breathing phase indicator is configured to display the desired motion signal as a waveform, wherein the breathing phase indicator is further configured to display the current motion signal as a location relative to the waveform.

6. The medical system of claim 1, wherein the breathing phase indicator is configured to display the desired motion signal as a location of a first object, wherein the breathing phase indicator is further configured to display the current motion signal as a position of a second object.

7. The medical system of claim 1, wherein the breathing phase indicator is configured to control an animation of a subject using the desired motion signal and the current motion signal.

8. The medical system of claim 1, wherein execution of the machine executable instructions further causes the processor to control the radiotherapy system with the control commands.

9. The medical system of claim 1, wherein the breath monitor system further comprises any one of the following: a respiratory belt, an optical respiratory detection system, an infra-red respiratory detection system, an internal navigator pulse sequence, and combinations thereof.

10. The medical system of claim 1, wherein the subject display is any one of the following: a projector configured to project the breath phase indicator on a wall, a projector configured to project the breath phase indicator on a bore of the medical system, a LCD display, and a magnetic resonance imaging compatible display.

11. The medical system of claim 1, wherein the radiotherapy system is any one of the following: a linear accelerator radiotherapy system, a cobalt radiotherapy system, and an X-ray radiotherapy system.

12. A method of operating a medical system, wherein the medical system comprises:
  a magnetic resonance imaging system;
  a radiotherapy system configured to controllably irradiate a target volume within an irradiation zone;
  a subject support configured to support at least a ventral region of a subject within the irradiation zone;
  a breath monitor system comprising a camera, the breath monitor system configured to provide a motion signal descriptive of subject breathing motion; and
  a subject display configured to display a breathing phase indicator to the subject supported by the subject support;
  wherein the method comprises:
  acquiring a measured motion signal with the breath monitor system for a predetermined duration;
  controlling the magnetic resonance imaging system with calibration pulse sequence commands to acquire calibration magnetic resonance data, wherein the calibration pulse sequence commands are configured to acquire calibration magnetic resonance data from an imaging zone according to a four-dimensional magnetic resonance imaging protocol, wherein the calibration magnetic resonance data is divided into movement phase bins, and
  wherein the method further comprises repeatedly:
  determining a temporary desired motion signal by temporally stepping through the measured motion signal;
  acquiring a calibration motion signal using the breath monitor system;
  bin the calibration magnetic resonance data into the movement phase bins using the calibration motion signal, and
  rendering the breathing phase indicator on the subject display, wherein the breathing phase indicator is configured to indicate a difference between the temporary desired motion signal and the calibration motion signal;
  wherein the method further comprises repeatedly:
  determining a desired motion signal by temporally stepping through the measured motion signal;
  acquiring a current motion signal using the breath monitor system;
  rendering the breathing phase indicator on the subject display, wherein the breathing phase indicator is configured to indicate a difference between the desired motion signal and the current motion signal; and
  generating control commands configured to control targeting of the radiotherapy system using a first portion of time resolved magnetic resonance imaging dataset synchronized to the desired motion signal or a second portion of the time resolved magnetic resonance imaging dataset referenced by the current motion signal wherein the control commands are selected between the first portion of the time resolved magnetic resonance imaging dataset and the second portion of the time resolved magnetic resonance imaging dataset by applying a predetermined criterion to a match between the current motion signal and the measured motion signal.

13. A tangible, non-transitory computer readable medium that stores machine executable instructions, which when executed by a processor, cause the processor to:
  acquire a measured motion signal with a breath monitor system for a predetermined duration;
  control a magnetic resonance imaging system with calibration pulse sequence commands to acquire calibration magnetic resonance data, wherein the calibration pulse sequence commands are configured to acquire the calibration magnetic resonance data from an imaging zone according to a four-dimensional magnetic resonance imaging protocol, wherein the calibration magnetic resonance data is divided into movement phase bins;
  determine a temporary desired motion signal by temporally stepping through the measured motion signal;
  acquire a calibration motion signal using the breath monitor system;
  bin the magnetic resonance imaging data into the movement phase bins using the calibration motion signal, and
  render a breathing phase indicator on a subject display, wherein the breathing phase indicator is configured to indicate a difference between the temporary desired motion signal and the calibration motion signal; and
  repeatedly: determine a desired motion signal by temporally stepping through the measured motion signal; acquire a current motion signal using the breath monitor system; render the breathing phase indicator on the subject display, wherein the breathing phase indicator is configured to indicate a difference between the desired motion signal and the current motion signal; and generate control commands configured to control targeting of a radiotherapy system using a first portion of a time resolved magnetic resonance imaging dataset synchronized to the desired motion signal or a second portion of the time resolved magnetic resonance imaging dataset referenced by the current motion signal wherein the control commands are selected between the first portion of the time resolved magnetic resonance imaging dataset and the second portion of the time resolved magnetic resonance imaging dataset by applying a predetermined criterion to a match between the current motion signal and the measured motion signal.

14. The tangible, non-transitory computer readable medium of claim 13, wherein the machine executable instructions further comprise imaging pulse sequence commands, which when executed by the processor, further cause the processor to:
- acquire imaging magnetic resonance data by controlling the magnetic resonance imaging system with the imaging pulse sequence commands during generation of the control commands; and
- reconstruct at least one magnetic resonance image from the imaging magnetic resonance data, wherein the breathing phase indicator is further configured to display the at least one magnetic resonance image.

15. The tangible, non-transitory computer readable medium of claim 13, wherein execution of the machine executable instructions further causes the processor to control a radiotherapy system with the control commands.

16. The medical system of claim 1, wherein the camera is an infra-red camera.

17. The method of claim 12, wherein the camera is an infra-red camera.

* * * * *